March 4, 1947. A. F. ETTER Plant Pat 723
APPLE TREE
Filed June 23, 1944
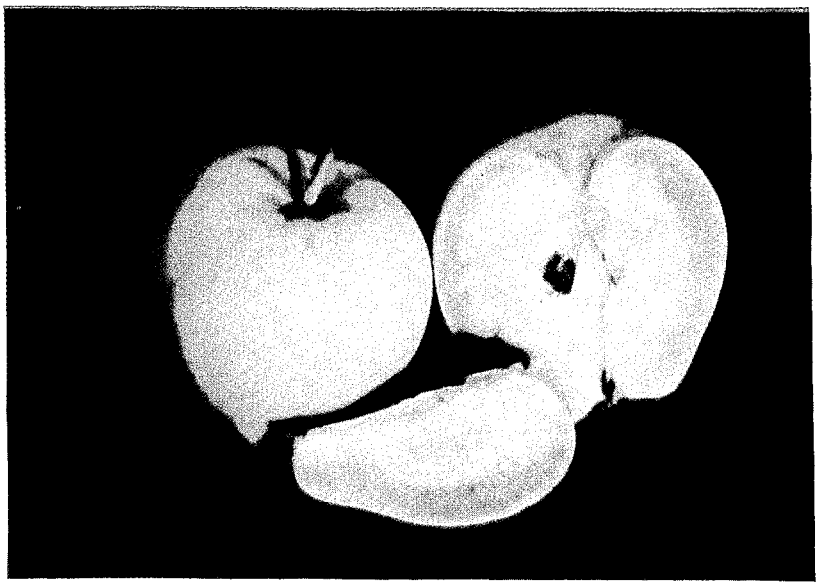
INVENTOR.
ALBERT F. ETTER.
BY
Chas. E. Townsend.
ATTORNEY.

Patented Mar. 4, 1947

Plant Pat. 723

UNITED STATES PATENT OFFICE

723

APPLE TREE

Albert F. Etter, Ettersburg, Calif., assignor to George C. Roeding, Jr., Niles, Calif.

Application June 23, 1944, Serial No. 541,691

1 Claim. (Cl. 47—62)

This invention relates to a new variety of apple tree characterized by its fruit having a transparent skin which glows with the color of the pink flesh beneath. The fruit is unique in color and partakes of the shape of a Bellflower apple.

In size, the fruit of this variety is comparable to the Northfield. The diameter of the apple varies from 2 inches up to 2¾ inches and even larger at times. A specimen of this apple has been known to measure 7 inches in circumference and 2½ inches in length.

The accompanying colored photograph illustrates this new discovery.

The following is a detail description of this new variety:

Stem of fruit: Long.
Calyx: Closed.
Basin: Small and shallow.
Skin: Transparent, showing pink from flesh beneath.
Calyx tube: Small.
Core: Small.

Seeds: Dark, medium size.
Flesh: Pink in color; crisp and juicy.
Foliage: Strong, medium sized, and abundant.
Origin: A seedling of "Surprise."

The fruit of this variety of apple tree ripens in September and is outstanding in its startling bouquet, discovered with the first bite into the fruit.

The new variety of apple tree differs from "Surprise" in that "Surprise" has a darker green foliage and a smoother leaf than does the new variety. Further, "Surprise" has less tomentum and a darker shade of pink blossom than does the new variety.

What I claim is:

A new variety of apple tree substantially as herein disclosed having strong, medium sized and abundant foliage and characterized by fruit having the shape of a Bellflower and the size of a Northfield, with transparent skin which glows with the color of the pink flesh beneath.

ALBERT F. ETTER.